(12) United States Patent
Xie

(10) Patent No.: US 11,969,457 B2
(45) Date of Patent: Apr. 30, 2024

(54) APPLICATION OF SKELETAL MUSCLE SECRETED FACTOR THBS4 IN PREPARATION OF DRUG FOR IMPROVING SYSTEMIC GLUCOSE AND LIPID METABOLISM

(71) Applicant: Institute of Microbiology, Guangdong Academy of Sciences(Guangdong Detection Center of Microbiology), Guangzhou (CN)

(72) Inventor: Liwei Xie, Guangzhou (CN)

(73) Assignee: Institute of Microbiology. Guangdong Academy of Sciences(Guangdong Detection Center of Microbiology), Guangzhou (CN)

( * ) Notice: Subject to any disclaimer, the term of this patent is extended or adjusted under 35 U.S.C. 154(b) by 0 days.

(21) Appl. No.: 18/062,028

(22) Filed: Dec. 6, 2022

(65) Prior Publication Data

US 2023/0398179 A1  Dec. 14, 2023

(30) Foreign Application Priority Data

Jun. 9, 2022 (CN) .......... 202210645318.X

(51) Int. Cl.
*A61K 38/00* (2006.01)
*A61K 38/17* (2006.01)
*A61P 3/00* (2006.01)

(52) U.S. Cl.
CPC ........... *A61K 38/1741* (2013.01); *A61P 3/00* (2018.01)

(58) Field of Classification Search
CPC .............................. A61K 38/1741; A61P 3/00
See application file for complete search history.

(56) References Cited

U.S. PATENT DOCUMENTS

2009/0220983 A1 * 9/2009 Archambault ....... C12Q 1/6886
435/7.92

FOREIGN PATENT DOCUMENTS

CN 110747229 A 2/2020

OTHER PUBLICATIONS

Ella G. Frolova, et al., Control of organization and function of muscle and tendon by thrombospondin-4, Matrix Biology, 2014, pp. 35-48, vol. 37.
NP_035712.1, thrombospondin-4 precursor [Mus musculus], Identical Proteins FASTA Graphics, 2022.

* cited by examiner

*Primary Examiner* — Jeanette M Lieb
(74) *Attorney, Agent, or Firm* — Bayramoglu Law Offices LLC

(57) ABSTRACT

An application of a skeletal muscle secreted factor Thbs4 in a preparation of a drug for improving systemic glucose and lipid metabolism is provided. According to the present invention, it is found through experiments that Thbs4 increases a body's metabolic rate by activating a beige-like change of white adipose, relieves the metabolic disorder caused by high-fat diet, and reveals its application value in the treatment of the metabolic disorder.

8 Claims, 8 Drawing Sheets

Specification includes a Sequence Listing.

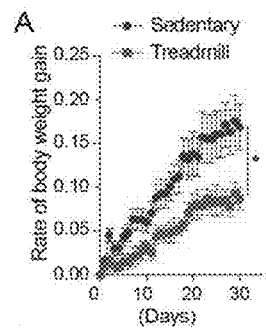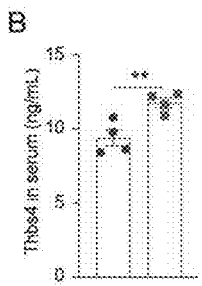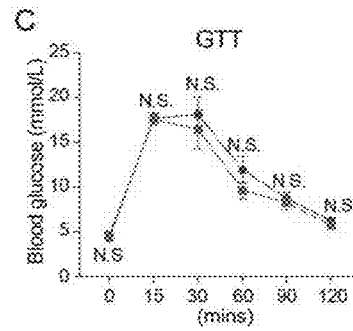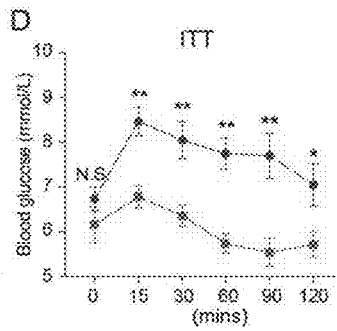
FIG. 1A  FIG. 1B  FIG. 1C  FIG. 1D
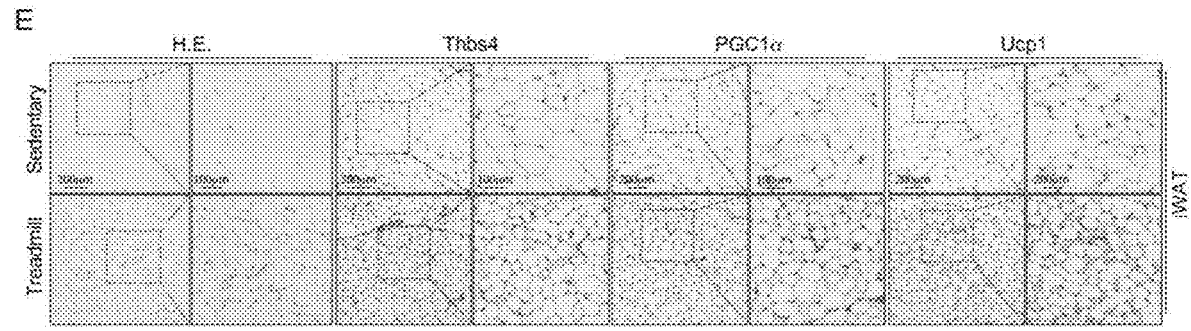
FIG. 1E
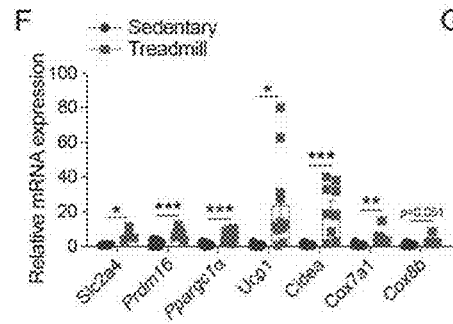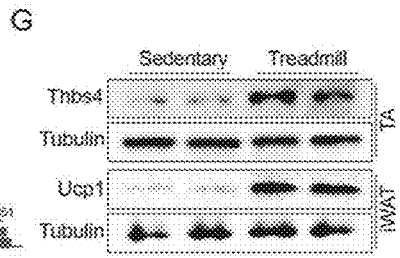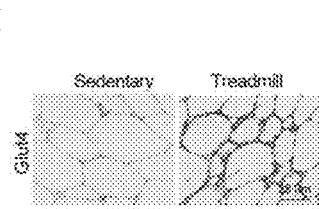
FIG. 1F  FIG. 1G  FIG. 1H

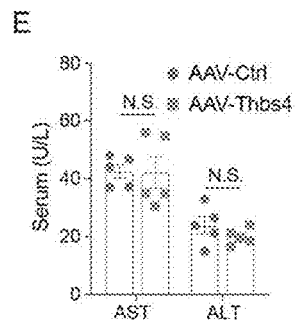
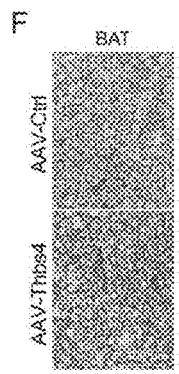
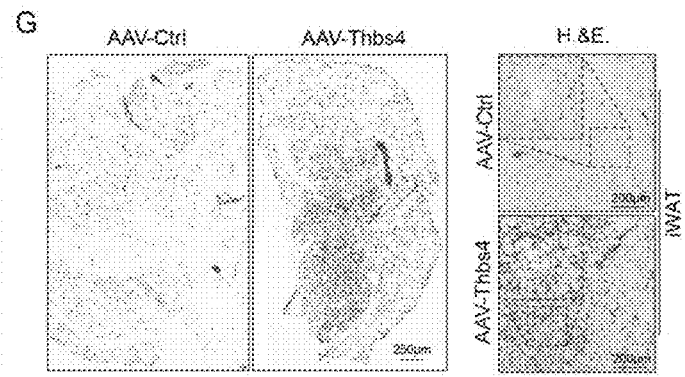
FIG. 4E　　FIG. 4F　　FIG. 4G
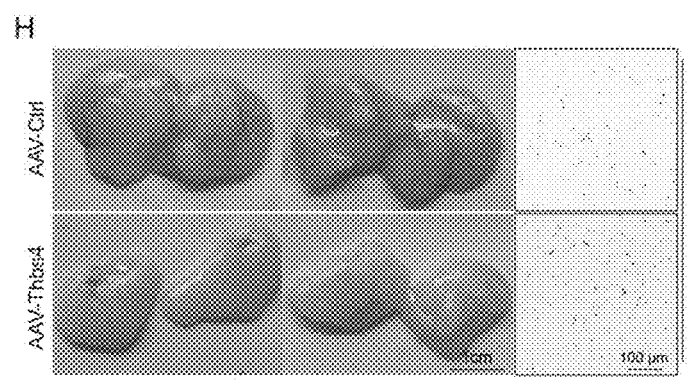
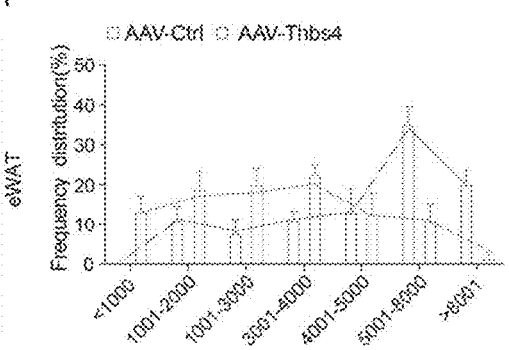
FIG. 4H　　　　　　　　　　FIG. 4I
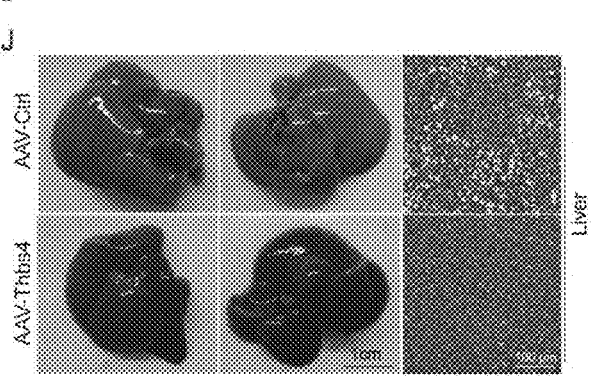
FIG. 4J

APPLICATION OF SKELETAL MUSCLE SECRETED FACTOR THBS4 IN PREPARATION OF DRUG FOR IMPROVING SYSTEMIC GLUCOSE AND LIPID METABOLISM

CROSS REFERENCE TO THE RELATED APPLICATIONS

This application is based upon and claims priority to Chinese Patent Application No. 202210645318.X, filed on Jun. 9, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBKY085_Sequence_Listing.xml, created on Nov. 28, 2022, and is 5,764 bytes in size.

TECHNICAL FIELD

The present invention belongs to the fields of biotechnology and metabolic biology, and more particularly relates to an application of a skeletal muscle secreted factor Thbs4 in the preparation of a macro-molecular drug (or a biological preparation) for improving systemic glucose and lipid metabolism.

BACKGROUND

Skeletal muscles account for about 40-50% of the total body weight in a healthy human body, are the largest organ in the human body, and play a vital role in daily physical activities. Exercising can achieve broad benefits on the host's health through a plurality of mechanisms, e.g., losing weight, improving cardiovascular functions, and maintaining a muscle mass, strength, and oxidative fiber type ratio. These changes in skeletal muscles due to exercising are associated with systemic benefits to distal organ physiology and metabolism through interorgan tandem. Upon recent researches, it is found that exercise-induced and skeletal muscle-derived metabolites or secreted factors, such as β-aminobutyric acid, γ-aminobutyric acid, interleukin-6, and irisin, exert positive effects on glucose, lipid, and energy metabolism locally and systemically. The present invention mainly provides data to find that an exercise-induced skeletal muscle secreted factor Thbs4 activates a beige-like change of white adipose by enriching on the surface of an inguinal white adipose membrane, thereby increasing a body's metabolic rate, and alleviating the metabolic disorder caused by high-fat diet.

SUMMARY

An objective of the present invention is to provide an application of a skeletal muscle secreted factor Thbs4 in the preparation of a drug for improving systemic glucose and lipid metabolism.

Preferably, the present invention provides an application of a skeletal muscle secreted factor Thbs4 in a drug for activating a beige-like change of white adipose, increasing a body's metabolic rate, and alleviating the metabolic disorder caused by high-fat diet.

Preferably, the skeletal muscle secreted factor Thbs4 is a recombinant skeletal muscle secreted factor Thbs4 protein having an amino acid sequence shown in SEQ ID NO: 1.

The amino acid sequence (963 amino acids) of the Thbs4 protein is specifically as follows:

```
  1 MPAPRAAAAA FLLLHLVLQP WQRTSAQATP QVFDLLPSSS QRLNPSALQP VLTDPTLHEV

61 YLISTEKLQS KSSATIFGLY SSSDNSKYFE FTVMGRLNKA ILRYLKNDGK IHLVVFNNLQ

121 LADGRRHRVL LRLSNLQRGD GSVELYLDCA QADSVRNLPR AFSGLTQNPE SIELRTFQRK

181 PQDFLEELKL VVRGSLFQVA SLQDCFLQQS EPLAATSTGD FNRQFLGQMT QLNQLLGEVK

241 DLLRQQVKET SFLRNTIAEC QACGPLSFQS PTPNTLVPIA PPAPPTRPTR HCDSSPCFRG

301 VRCTDTRDGF QCGPCPDGYT GNGITCSDVD ECKYHPCYPG VRCVNLAPGF RCDACPVGFT

361 GPMVQGVGIN FAKTNKQVCT DVDECQNGAC VLNSICINTL GSYRCGPCKP GYTGDQTRGC

421 KTERSCRNPE QNPCSVHAQC IEERQGDVTC VCGVGWAGDG YVCGKDVDID SYPDEELPCS

481 ARNCKKDNCK YVPNSGQEDA DRDGIGDACD EDADGDGILN EQDNCVLTHN IDQRNSDKDI

541 FGDACDNCRM VLNNDQKDTD GDGRGDACDD DMDGDGIKNI LDNCPRVPNR DQQDRDGDDV

601 GDACDSCPDV SNPNQSDVDN DLVGDSCDTN QDSDGDGHQD STDNCPTVIN SSQLDTDKDG

661 IGDECDDDDD NDGIPDLVPP GPDNCRLVPN PAQEDSNNDG VGDICEADED QDQVIDHIDV

721 CPENAEITLT DFRAYQTVVL DPEGDAQIDP NWVVLNQGME IVQTMNSDPG LAVGYTAFNG

781 VDFEGTFHVN TQTDDDYAGF IFGYQDSSSF YVVMWKQTEQ TYWQATPFRA VAEPGIQLKA

841 VKSKTGPGEH LRNSLWHTGD TSDQVRLLWK DSRNVGWKDK VSYRWFLQHR PQVGYIRVRF

901 YEGSELVADS GVTIDTTMRG GRLGVFCFSQ ENIIWSNLKY RCNDTIPEDF QEFQTQSFDR

961 LDN.
```

Preferably, the skeletal muscle secreted factor Thbs4 is an expression vector secreting the skeletal muscle secreted factor Thbs4, such as an adeno-associated virus expressing Thbs4.

Preferably, the Thbs4 recombinant protein induces the expression of genes related to mitochondrial metabolism and thermogenesis in C3H10/T2 or primary white adipocytes (SVF) in vitro.

A second objective of the present invention is to provide a drug for improving a systemic glucolipid metabolism, which contains a skeletal muscle secreted factor Thbs4 or an expression vector that secretes the skeletal muscle secreted factor Thbs4.

According to the present invention, upon experiments, it is found that Thbs4 increases a body's metabolic rate by activating the beige-like change of white adipose, alleviates the metabolic disorder caused by high-fat diet, and reveals its application value in the treatment of the metabolic disorder.

BRIEF DESCRIPTION OF THE DRAWINGS

FIGS. 1A-1K show the expression of Thbs4 in skeletal muscles and the changes of related proteins in serum and adipocytes;

FIGS. 3A-3H and FIGS. 4A-4J are diagrams of changes in respective indexes and related proteins after 16 weeks of high-fat diet feeding in C57BL/6J mice intramuscularly injected with AAV-Ctrl or AAV-Thbs4.

DETAILED DESCRIPTION OF THE EMBODIMENTS

Figures 1I, 1J, 1K:
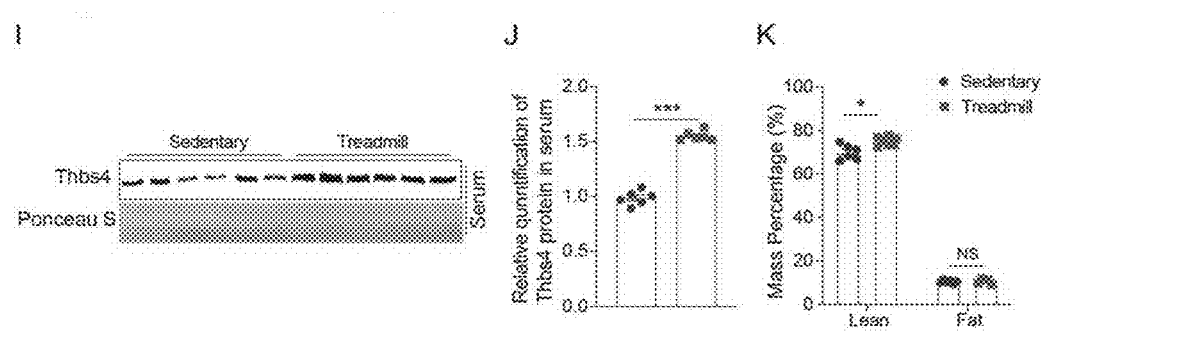

The following embodiments are used to further describe the present invention, rather than limiting the present invention.

Embodiment 1

I. Experimental Method

1. Animal feeding and experiment: C57BL/6J mice are purchased from Guangzhou University of Traditional Chinese Medicine Animal Center or Guangdong Laboratory Animal Center. To induce a Thbs4 protein level externally, an AAV9-Thbs4-HA (Genechem gene) virus is injected intra-muscularly into TA muscles to induce Thbs4 overexpression in skeletal muscles. To assess a Thbs4 level in serum, blood is collected from the caudal vein and subjected to Western blot confirmation with an HA antibody. These experimental animals are housed in an animal facility of the Institute of Microbiology, Guangdong Academy of Sciences under a 12-hour light/12-hour dark cycle (7:00 am-7:00 pm) at a temperature of 23±2° C. with free access to food and water from a standard irradiated rodent feed. For a diet-induced obesity (DIO)-related experiment, 6-week-old mice (having a body weight of about 15 g) are fed with high-fat diet (containing 60% of adipose) for at least 15 weeks. All animal handling and procedures are approved by the Animal Care and Use Committee of the Guangdong Institute of Microbiology [License number: GT-IACUC201704071].

2. Mouse exercise on treadmill: C57BL6/J mice do a regular aerobic exercise for 1 hour a day, 5 days a week with the help of a standardized mouse treadmill that can adjust a speed automatically, and a program is set in a mode of increasing a speed by 2 m/min every 20 min (10 m/min pre-run for 30 min to adapt to the environment). A runway is disposed horizontally with no slope. Resting mice are taken as controls.

3. Glucose tolerance (GTT) and insulin (ITT) sensitivity tests: the GTT of ITT test is used to measure a blood glucose level with Yuyue 306 by using blood collected from the caudal vein. Therefore, mice are fasted for 16 hours (GTT: 6:00 pm-10:00 am) or 6 hours (ITT: 8:00 am-2:00 pm) before each experiment. A fasting blood glucose level is measured and designated as an initial blood glucose level. For GTT, experimental mice are injected intraperitoneally with 20% D-glucose (2 g/kg fasting body weight), followed by quantification of the blood glucose level at 15, 30, 60, 90, and 120 minutes after injection. For ITT, mice are injected intraperitoneally with insulin (VL7516, Eli Lilly and Company (0.75 U/kg body weight). Caudal blood glucose levels are measured at different time points (15, 30, 60, 90 and 120 minutes) after intraperitoneal injection.

4. Immunohistochemical staining: an adipose tissue is embedded in paraffin, sectioned at 4 μm, and mounted on a polylysine-coated glass slide. A paraffin section is degreased in xylene, hydrated sequentially in 100%, 90%, 80%, 70%, and 50% ethanol, and then rinsed ddH$_2$O. Antigen retrieval is performed by boiling the section for 1 hour in Tris-EDTA buffer (1.21 g of Tris and 0.37 g of EDTA are dissolved in 1 L ddH$_2$O, a pH of 9.0). After cooling for 1 hour to room temperature, the section is washed twice with PBS for 5 minutes each. The section is permeabilized in PBS containing 0.2% of Triton X-100 for 10 minutes. The section is incubated in 3% H$_2$O$_2$ PBS for 10 minutes. After washing with PBS, the section is blocked with 5% of normal goat serum 3% BSA for 1 hour at room temperature, and then incubated overnight at 4° C. with a primary antibody against Glut4 (1:200, Abclonal), Ucp1 (1:500, Abcam) and Thbs4 (1:200, Abclonal) in 3% BSA containing 5% of normal goat serum. After overnight incubation, the section is washed for 3 times with PBS, incubated with a 1:500 goat anti-rabbit secondary antibody in 3% BSA containing 5% of normal goat serum for 1 hour at room temperature, and then incubated with a DAB reagent (Sigma) for 3-5 minutes. The section is counterstained with a hematoxylin solution for 2 seconds, dehydrated, and sealed by using a Permount mounting medium (Sigma-Aldrich).

5. RNA extraction, revere transcription and fluorescent quantitation PCR: total RNA is extracted from tissues including skeletal muscle, iWAT, iBAT or liver by using a TRIzol™ reagent (Thermo Fisher). A RNA concentration is measured with a NanoDrop Absorbance Meter (Thermo Fisher) on a QuantStudio 6 Flex Real-Time PCR System (Thermo Fisher), reverse transcribed is performed by using 5× All-In-One Master Mix (G490, AbmGood), and gene expression is analyzed by using Power SYBR Green Master Mix (A25778, Applied Biosystems). The expression of a single gene is normalized to that of 18S ribosomal RNA, and thus this gene is a housekeeping gene (Thbs4 qPCR forward primer: 5'-GCAAATACCATCCCTGC-TATCC-3', as shown in SEQ ID No: 2; reverse primer: 5'-CCTCGTCTGATCACCAGTGTAC-3', as shown in SEQ ID NO: 3).

6. Immunoblotting: a tissue (such as skeletal muscle, iWAT, iBAT) is homogenized in RIPA buffer, wherein the buffer contains 150 mM of NaCl, 1% of NP-40, 0.1% of SDS, 25 mM of Tris-HCl (pH 7.4), 0.5% of odium deoxycholate, and 1× of complete proteasome inhibitor cocktail (Thermo Scientific). A protein concentration is measured by using a Pierce™ BCA Protein Assay Kit (Thermo Fisher). A protein is isolated by using SDS-polyacrylamide gel electrophoresis (PAGE) and transferred to a PVDF membrane (Merck Millipore). The protein on the membrane is blocked with 5% (w/v) defatted milk for 1 hour at room temperature, and then processed with a primary antibody. An image is visualized by using an ECL reagent (Thermo Fisher Scientific). The image is acquired with a ChemiDoc™ imaging system (Bio-Rad).

7. Isolation, culture and differentiation of primary white adipocytes: C3H10/T2 inguinal white adipose tissue is dissected, minced, and digested for 30 minutes at 37° C. in PBS containing Collagenase II (1.5 mg/mL), Dispase II (2.4 U/mL) and $CaCl_2$ (10 mM). A tissue suspension is filtered through a 40 μm cell filter and centrifuged at 1000 g for 10 minutes to pelletize a stromal vascular fraction (SVF), and resuspended in a growth medium (DMEM containing 10% of fetal bovine serum (FBS)). Cells are plated on a collagen-coated flat plate overnight before culturing. Adipocytes are cultured to 100% confluence. Primary cells are grown for 3 days in an induction medium (DMEM containing 10% of FBS, 0.5 mM of isobutylmethyl-xanthine (IBMX), 125 m of indomethacin, 1 μM of dexamethasone, and 0.5 μM of rosiglitazone), followed by growth for 7 days in a differentiation medium (DMEM containing 10% of FBS, 1 M of insulin, and 1 nM of triiodothyronine).

II. Experimental Results

1. Exercise Induces the Secretion of a Skeletal Muscle Secreted Factor Thbs4.

The changes in Thbs4 expression in skeletal muscles and protein serum and adipocytes during aerobic exercise on a treadmill compared to resting mice are shown. Thirty days after aerobic training gain is attenuated and the insulin sensitivity test (ITT) is improved, but the glucose tolerance test (GTT) is not significantly different (FIGS. 1A-1D). Aerobic exercise also increases Thbs4 level in serum, followed by membrane enrichment on beige adipocytes, which are also stained by Ucp1 and PGC1 (FIG. 1E). Aerobic exercise induces a beige-like change in iWAT and up-regulates thermogenesis-related genes (such as Prdm16, Ucp1, Ppargc1, Cidea, Cox7a1, and Cox8b), accompanied by an increase in Ucp1 protein level in iWAT and the enrichment of a Glut4 protein on an iWAT membrane (FIGS. 1F-1H). Long-term aerobic exercise induces increased expression of the Thbs4 protein in skeletal muscles and secretion into serum (FIGS. 1G, 1I-1J), accompanied by an increase in muscle percentage, but no significant change in adipose mass (FIG. 1K). In conformance to aerobic exercise data, Thbs4 may act as an exercise-induced skeletal muscle-specific secreted protein to mimic the metabolic benefits of exercise or muscle hypertrophy.

2. The Expression of Thbs4 Overexpressed by an AAV Virus Promotes the Beige-Like Change of White Adipose.

Figures 2A, 2B, 2C, 2D:
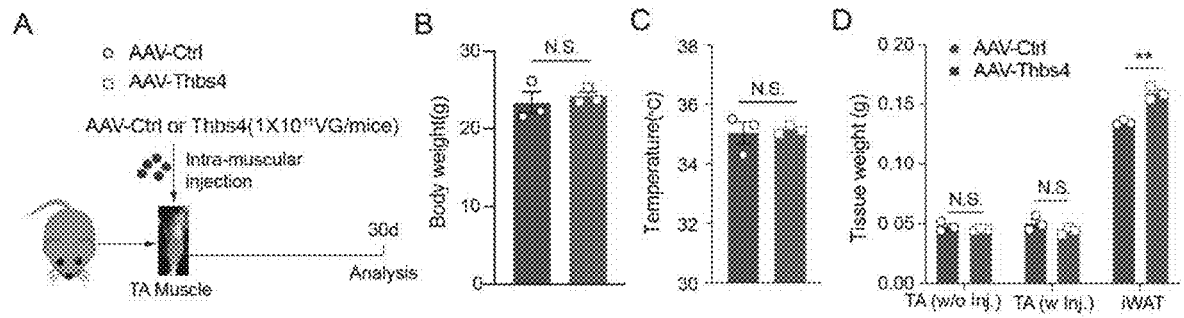
FIGS. 2A-2H are result diagrams that the expression of Thbs4 overexpressed by an AAV virus promotes a beige-like change of white adipose.
Figures 2E, 2F, 2G:
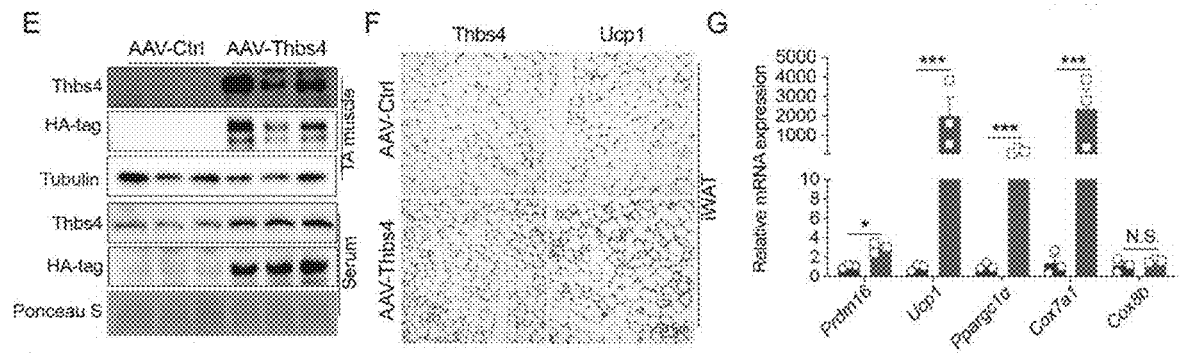
Figure 2H:
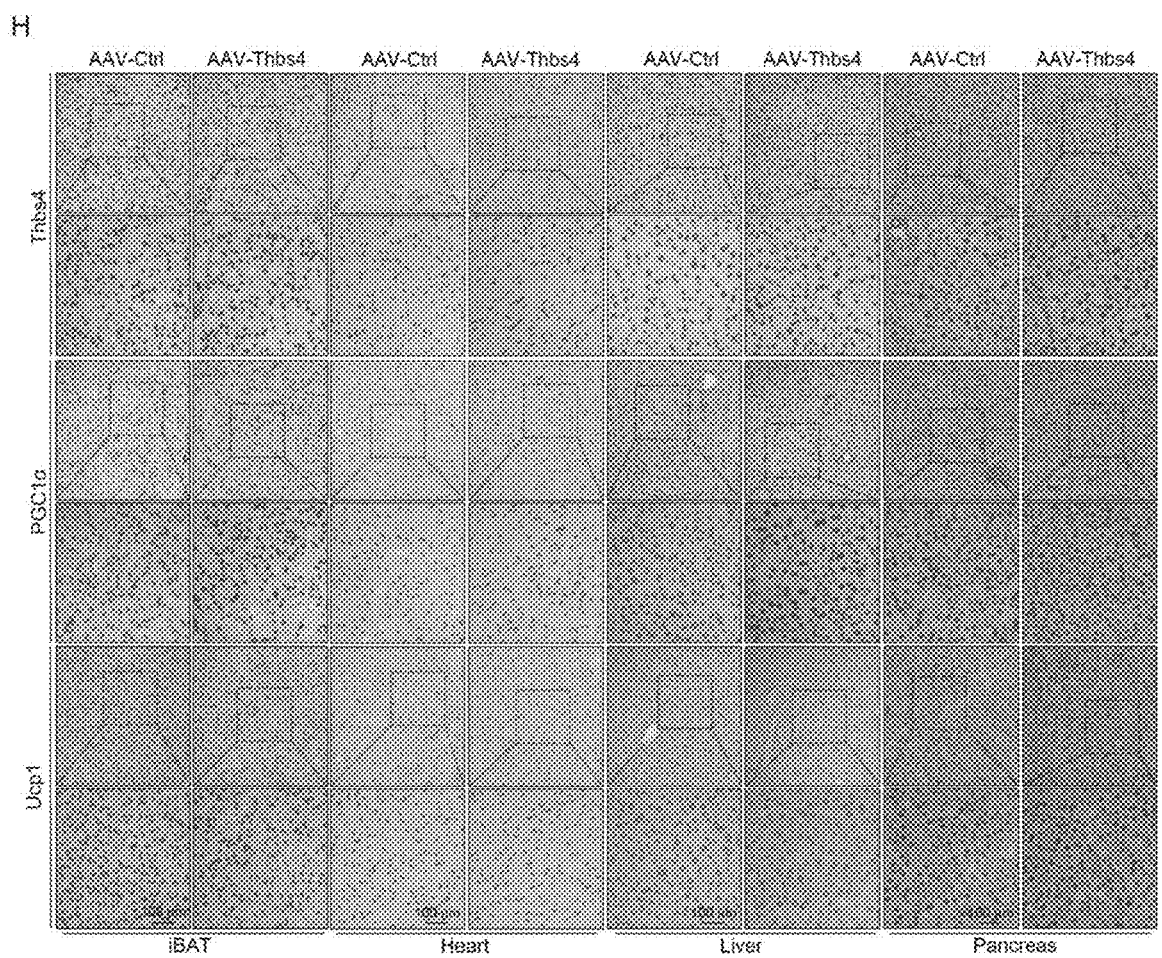

To explore the beneficial effects a Thbs4 on systemic metabolic homeostasis, Thbs4 is over-expressed in muscles by intramuscular injection of an adeno-associated virus (AAV-Thbs4) expressing Thbs4 to mice to induce the Thbs4 level in serum (FIG. 2A). Thirty days after AAV-Thbs4 injection, except for a slight increase in iWAT weight, no significant difference is reflected in body weight, rectal temperature, and TA muscle weight between an AAV-Ctrl group and an AAV-Thbs4 group (FIGS. 2B-2D). Intramuscular injection of AAV-Thbs4 results in overexpression of the Thbs4 protein in TA muscles (detected with HA and Thbs4 antibodies) and induces externally expressed HA-tagged Thbs4 in serum (FIG. 2E). AAV-Thbs4 also increases membrane enrichment of Thbs4 in iWAT, while increasing the Ucp1 expression in a multicellular lipid droplet region and up-regulation of thermogenesis-related genes (FIGS. 2F-2G). To assess whether the externally expressed Thbs4 is localized to tissues other than iWAT, IHC of iBAT, heart, liver and pancreas against Thbs4, PGC1 and Ucp1 shows that Thbs4 expressed externally by skeletal muscles is not enriched in these tissues (FIG. 2H). These data further demonstrate that the externally expressed Thbs4 activates the beige-like change of white adipose only by enrichment on a cell membrane of iWAT.

3. Thbs4 has Long-Term Protection Against a Metabolic Syndrome.

Figure 3A:
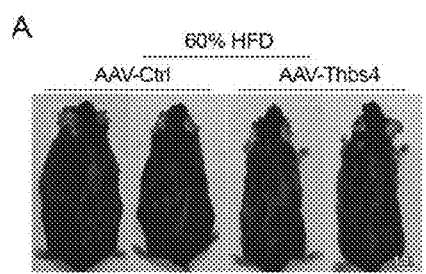
Figure 3B:
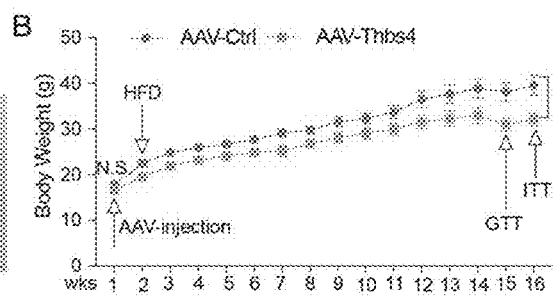
Figure 3C:
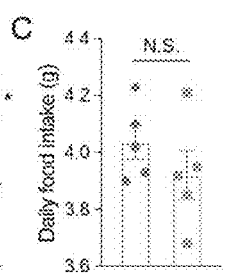
Figure 3D:
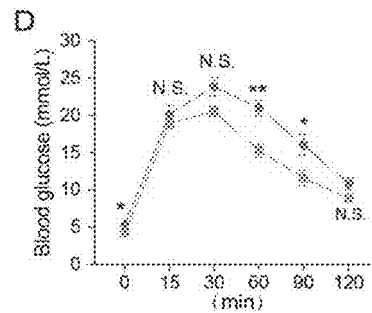
Figure 3E:
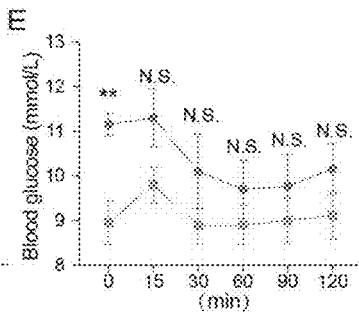
Figure 3F:
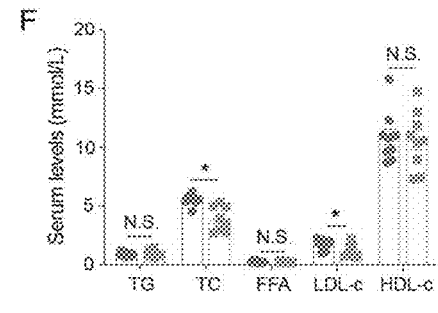
Figure 3G:
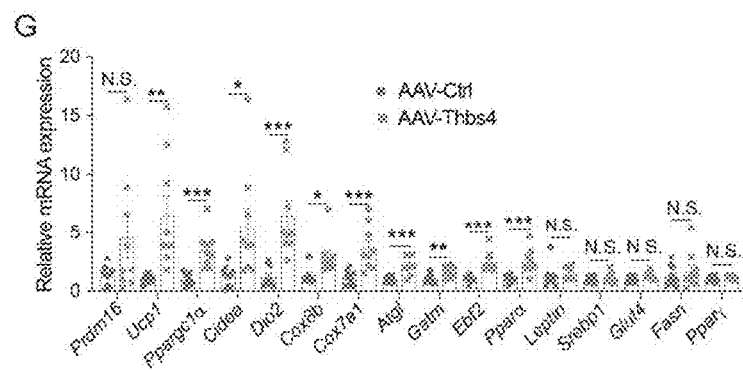
Figure 3H:
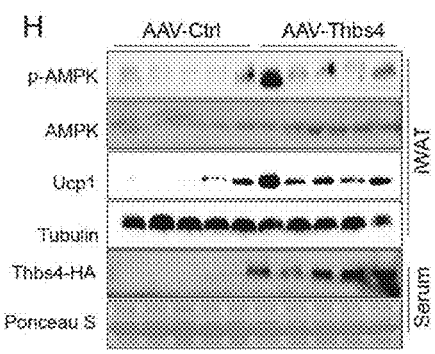
Figure 4A:
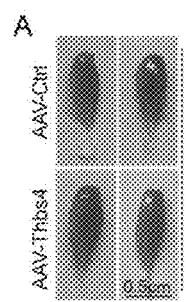
Figure 4B:
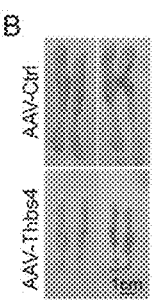
Figure 4C:
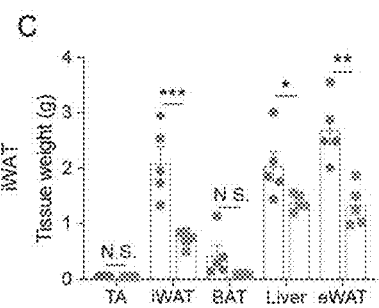
Figure 4D:
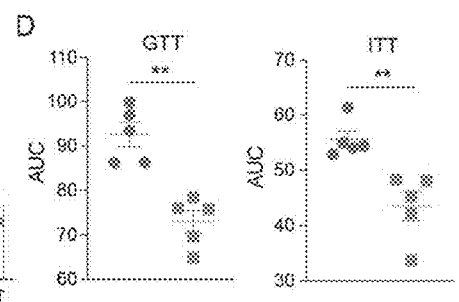

To further explore the long-term protective role of Thbs4, C57BL/6J mice intramuscularly injected with AAV-Ctrl or AAV-Thbs4 are fed with a high-fat diet for 16 weeks. The high serum Thbs4 level shows a significant protective effect on HFD, resulting in a decrease in body weight, adipose mass (iWAT and eWAT), and liver weight, showing a significant difference therebetween, but no significant difference in food intake (FIGS. 3A-3C, FIGS. 4A-4C). An AAV-Thbs4 injection group is also characterized by improved glucose tolerance (GTT) and insulin sensitivity (ITT) (FIGS. 3D-3E, FIG. 4D). Serum lipid analysis indicates that a higher Thbs4 serum level results in lower serum TC and LDL-c (FIG. 3F). Serum TG, FFA, HDL-c, ALT, and AST levels are similar between the two groups (FIG. 3F and FIG. 4E). Notably, the AAV-Thbs4 group exhibits higher expression levels of thermogenesis-related genes, such as Prdm16, Ppargc1a, Ucp1 Cidea, Dio2, Cox7a1, Cox8b, Gatm, Ppar, and Ebf2, as well as lipolysis-related genes, such as Atgl (FIG. 3G). Furthermore, the high serum level of Thbs4 increases Ucp1 and p-AMPK protein levels (FIG. 3H). H&E staining indicates that the two groups display similar phenotypes on iBAT, but the AAV-Thbs4 group has long-term and systemic protection in the induction of iWAT and eWAT in white adipocytes and lipid clearance in the liver (FIGS. 4F-4J).

4. A Thbs4 Recombinant Protein Activates the Mitochondrial Metabolism of Adipocytes In Vitro.

Figure 5A:
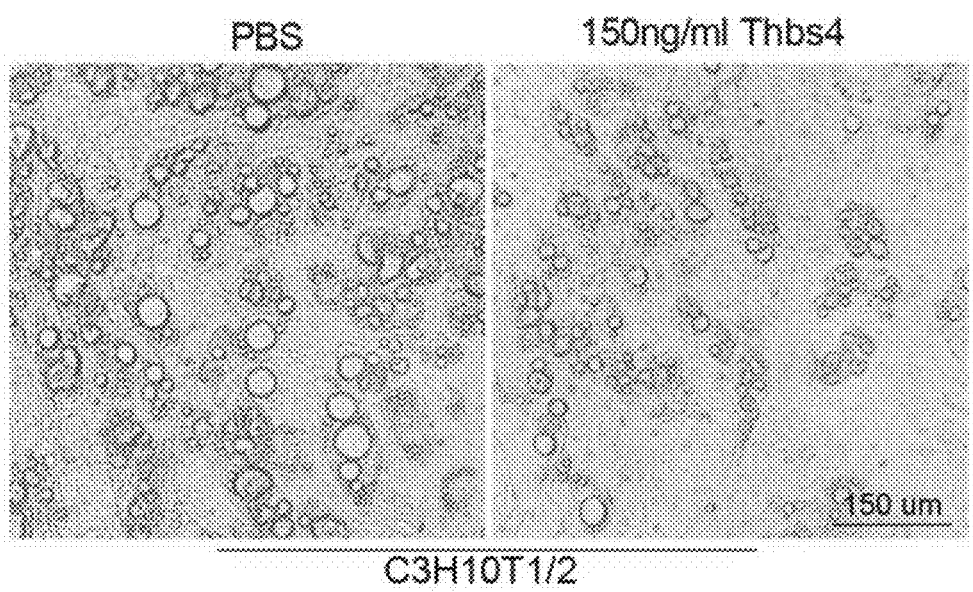
FIGS. 5A-5F show that a Thbs4 recombinant protein that activates a mitochondrial metabolism of adipocytes in vitro.
Figure 5B:
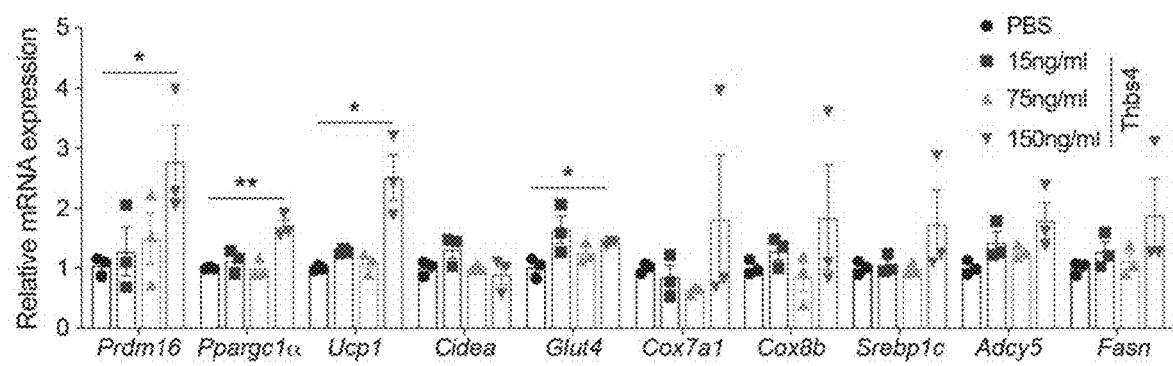
Figure 5C:
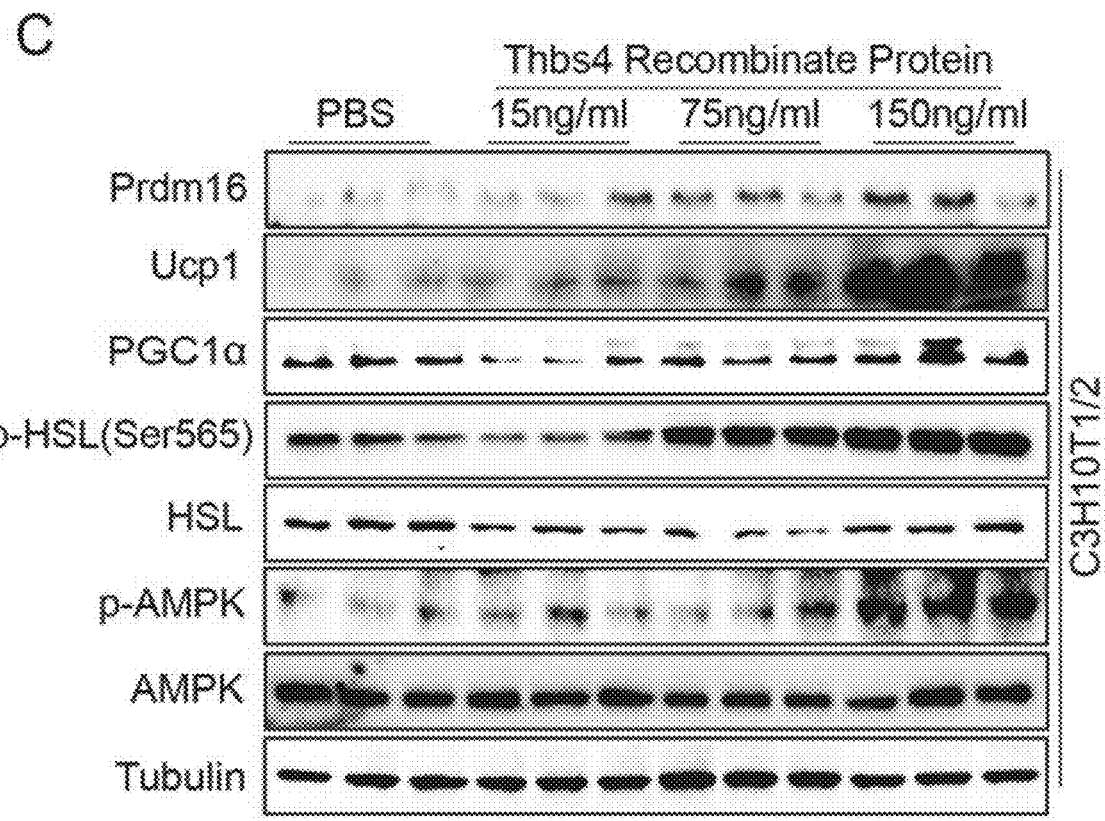
Figure 5D:
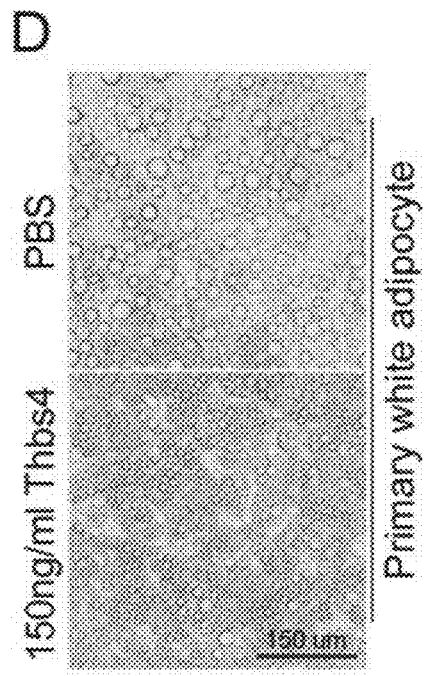
Figure 5E:
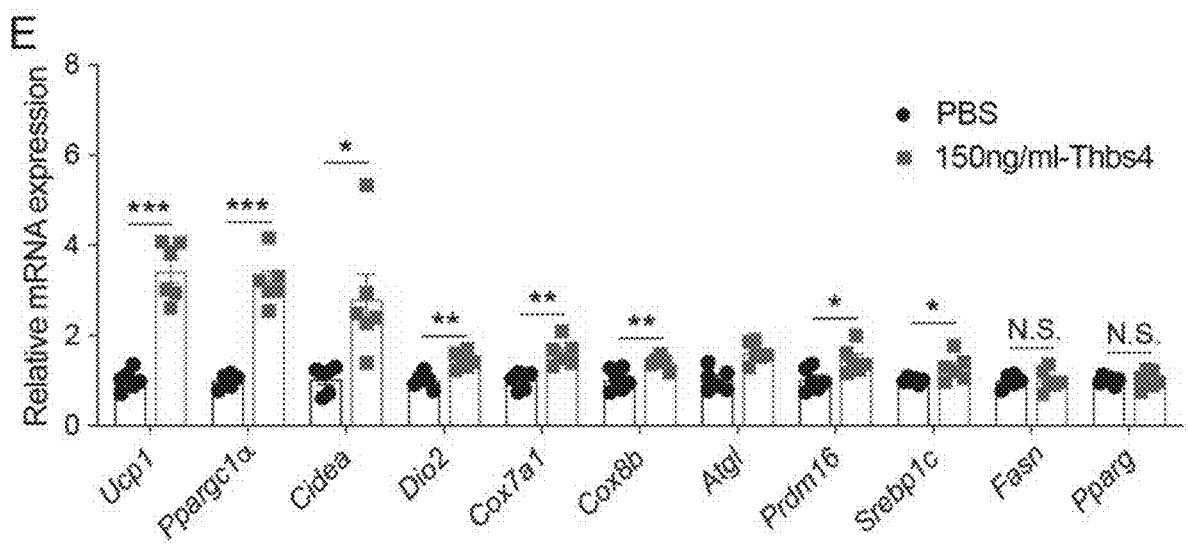
Figure 5F:
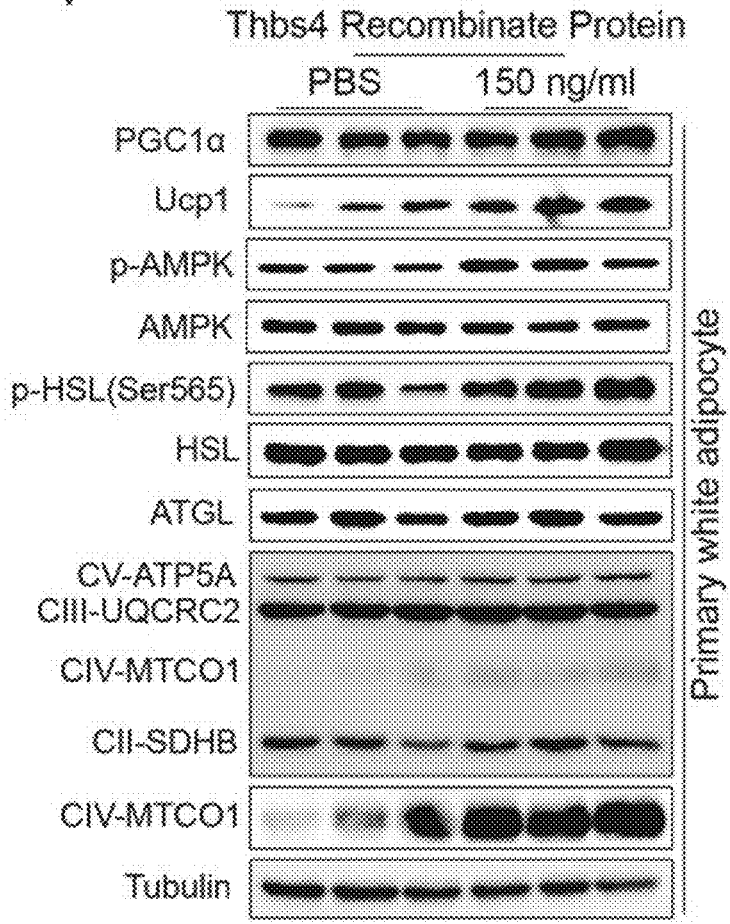

In vitro data also shows that the Thbs4 recombinant protein induces the expression of thermogenesis-related and lipolysis-related genes in a dose-dependent manner. A minimum of 150 ng/ml of Thbs4 recombinant protein activates the expression of Prdm16, Ucp1, Ppargc1 and Glut4 in C3H10/T2 cells (FIG. 5A). The protein levels of Prdm16, Ucp1, PGC1, p-HSL (Ser565) and p-AMPK also gradually increase in a dose-dependent manner (FIG. 5C). Similar observations are made in primary adipocytes differentiated from stromal vascular fractions (SVFs). The recombinant Thbs4 protein (150 ng/ml) up-regulates the expression of thermogenic genes (FIGS. 5D-5E) and slightly increases Ucp1, p-AMPK, p-HSL and mitochondrial complexes (FIG. 5F). In summary, these results demonstrate that Thbs4 has a protective effect on high-fat diet-induced metabolic disorders by promoting the activation of beige adipocytes of mice, revealing its application value in the treatment of metabolic disorders.

What is claimed is:

1. A method of improving systemic glucose and lipid metabolism in a subject comprising a step of intramuscular injection in the subject of an expression vector that expresses a recombinant skeletal muscle secreted factor Thbs4 protein in the subject, wherein the recombinant skeletal muscle secreted factor Thbs4 protein has the amino acid sequence shown in SEQ ID NO: 1.

2. The method according to claim 1, wherein expressing the recombinant skeletal muscle secreted factor Thbs4 protein in the subject activates a beige-like change of white adipose tissue in the subject, increases a metabolic rate in the subject, and alleviates a metabolic disorder in the subject caused by a high-fat diet.

3. The method according to claim 1, wherein the recombinant skeletal muscle secreted factor Thbs4 protein activates an expression of genes related to mitochondrial metabolism, thermogenesis in C3H10T/2, and metabolism of primary white adipocytes.

4. The method according to claim 1, wherein the expression vector that expresses the skeletal muscle secreted factor Thbs4 protein is an adeno-associated virus comprising a gene that expresses the recombinant skeletal muscle secreted factor Thbs4 protein.

5. A drug for improving a systemic glucolipid metabolism in a subject, comprising an expression vector comprising a gene for expression of recombinant skeletal muscle secreted factor Thbs4 protein, wherein the recombinant skeletal muscle secreted factor Thbs4 protein has the amino acid sequence shown in SEQ ID NO: 1.

6. The drug according to claim 5, wherein the expression vector that expresses the skeletal muscle secreted factor Thbs4 protein is an adeno-associated virus comprising a gene that expresses Thbs4.

7. The drug according to claim 5, wherein the drug is configured for intramuscular injection.

8. The method according to claim 1, wherein the recombinant protein skeletal muscle secreted factor Thbs4 protein is expressed in the subject at a concentration of 150 ng/ml.

* * * * *

SEQUENCE LISTING

```
Sequence total quantity: 3
SEQ ID NO: 1            moltype = AA   length = 963
FEATURE                 Location/Qualifiers
REGION                  1..963
                        note = The sequence is synthetized.
source                  1..963
                        mol_type = protein
                        organism = synthetic construct
SEQUENCE: 1
MPAPRAAAAA FLLLHLVLQP WQRTSAQATP QVFDLLPSSS QRLNPSALQP VLTDPTLHEV  60
YLISTFKLQS KSSATIFGLY SSSDNSKYFE FTVMGRLNKA ILRYLKNDGK IHLVVFNNLQ 120
LADGRRHRVL LRLSNLQRGD GSVELYLDCA QADSVRNLPR AFSGLTQNPE SIELRTFQRK 180
PQDFLEELKL VVRGSLFQVA SLQDCFLQQS EPLAATSTGD FNRQFLGQMT QLNQLLGEVK 240
DLLRQQVKET SFLRNTIAEC QACGPLSFQS PTPNTLVPIA PPAPPTRPTR HCDSSPCFRG 300
VRCTDTRDGF QCGPCPDGYT GNGITCSDVD ECKYHPCYPG VRCVNLAPGF RCDACPVGFT 360
GPMVQGVGIN FAKTNKQVCT DVDECQNGAC VLNSICINTL GSYRCGPCKP GYTGDQTRGC 420
KTERSCRNPE QNPCSVHAQC IEERQGDVTC VCGVGWAGDG YVCGKDVDID SYPDEELPCS 480
ARNCKKDNCK YVPNSGQEDA DRDGIGDACD EDADGDGILN EQDNCVLTHN IDQRNSDKDI 540
FGDACDNCRM VLNNDQKDTD GDGRGDACDD DMDGDGIKNI LDNCPRVPNR DQQDRDGDDV 600
GDACDSCPDV SNPNQSDVDN DLVGDSCDTN QDSDGDGHQD STDNCPTVIN SSQLDTDKDG 660
IGDECDDDDD NDGIPDLVPP GPDNCRLVPN PAQEDSNNDG VGDICEADFD QDQVIDHIDV 720
CPENAEITLT DFRAYQTVVL DPEGDAQIDP NWVVLNQGME IVQTMNSDPG LAVGYTAFNG 780
VDFEGTFHVN TQTDDDYAGF IFGYQDSSSF YVVMWKQTEQ TYWQATPFRA VAEPGIQLKA 840
VKSKTGPGEH LRNSLWHTGD TSDQVRLLWK DSRNVGWKDK VSYRWFLQHR PQVGYIRVRF 900
YEGSELVADS GVTIDTTMRG GRLGVFCFSQ ENIIWSNLKY RCNDTIPEDF QEFQTQSFDR 960
LDN                                                              963

SEQ ID NO: 2            moltype = DNA  length = 22
FEATURE                 Location/Qualifiers
misc_feature            1..22
                        note = The sequence is synthetized.
source                  1..22
                        mol_type = other DNA
                        organism = synthetic construct
SEQUENCE: 2
gcaaatacca tccctgctat cc                                          22

SEQ ID NO: 3            moltype = DNA  length = 22
FEATURE                 Location/Qualifiers
misc_feature            1..22
                        note = The sequence is synthetized.
source                  1..22
                        mol_type = other DNA
                        organism = synthetic construct
SEQUENCE: 3
cctcgtctga tcaccagtgt ac                                          22
```